United States Patent [19]
Fiedler et al.

[11] Patent Number: 5,844,147
[45] Date of Patent: Dec. 1, 1998

[54] METHOD AND APPARATUS FOR WATER SAMPLING UTILIZING SOLID PHASE EXTRACTION

[75] Inventors: Robert R. Fiedler, Lincoln; Dale A. Davison, Greenwood, both of Nebr.

[73] Assignee: ISCO, Inc., Lincoln, Nebr.

[21] Appl. No.: 814,950

[22] Filed: Mar. 10, 1997

[51] Int. Cl.[6] .................................................. G01N 1/18
[52] U.S. Cl. .................................................... 73/863.21
[58] Field of Search ........................... 73/863.02, 863.21, 73/863.23, 864.73, 846.34, 863.83, 61.55, 61.56; 210/661, 662, 767, 97, 416.1

[56] References Cited

U.S. PATENT DOCUMENTS

| | | | |
|---|---|---|---|
| 4,287,763 | 9/1981 | Richard | 73/863.21 |
| 4,713,974 | 12/1987 | Stone | 73/61.55 |
| 5,167,802 | 12/1992 | Sandstrom et al. | 210/134 |
| 5,531,106 | 7/1996 | Lyon et al. | 73/61.56 |

*Primary Examiner*—Robert Raevis
*Attorney, Agent, or Firm*—Henderson & Sturm

[57] ABSTRACT

A method and apparatus for water sampling utilizing on-site solid phase extraction that permits high sample flow rates and eliminates the requirement for sample storage. Samples are collected at a relatively high flow rate and then temporarily stored under pressure before passing through a solid phase extraction device at a slower rate commensurate with the flow rate tolerance of the device. Each sample quantity is also automatically measured, eliminating the requirement for sample storage and subsequent manual quantity measurement and/or transportation to a laboratory.

2 Claims, 6 Drawing Sheets

METHOD AND APPARATUS FOR WATER SAMPLING UTILIZING SOLID PHASE EXTRACTION

BACKGROUND OF THE INVENTION

1. Field of the Invention

This invention relates to water samplers, and more particularly to automatic water samplers utilizing on-site solid phase extraction for removing analytes from samples of interest.

2. Description of the Related Art

Sampling of rivers, lakes, wells, and wastewater systems for various contaminants such as pesticides is a well known way of monitoring the pollution of our natural resources. Prior art environmental sampling and analysis involves collecting large quantities of water sample in the field and then transporting the samples to a laboratory for subsequent analysis by liquid—liquid extraction. Liquid—liquid extraction, which requires the use of significant quantities of hazardous and expensive organic solvents that must be properly discarded after use, is generally been replaced by solid phase extraction. Solid phase extraction involves passing the water sample through a sorbent bed or membrane and then washing the trapped analyses from the bed or membrane with a much smaller quantity of solvent for subsequent analysis. Laboratory extraction and analysis, however, still requires that large quantities of samples be collected and then refrigerated or iced to prevent sample degradation prior to and during transportation to the laboratory. U.S. Pat. No. 5,167,802 issued to Sandstrom et al. attempts to alleviate the degradation problem by accomplishing the solid phase extraction in the field, at the time of sampling. Unfortunately, the shipment of large quantities of collected water to the laboratory is still required to determine sampling volumes. Further, the solid phase extraction apparatus of the '802 patent limits the sampling rate to the maximum flow rate of the extraction cartridge or membrane in use.

BRIEF SUMMARY OF THE INVENTION

The present invention relates to a method for water sampling utilizing on-site solid phase extraction that permits high sample collection rates and eliminates the requirement for sample storage and subsequent transportation to the laboratory. Samples are collected at a relatively high flow rate and then temporarily stored under pressure before passing through a solid phase extraction device at a slower rate commensurate with the devices flow rate tolerance. Each sample quantity is also automatically measured, eliminating the requirement for sample storage and subsequent manual quantity measurement and/or transportation to a laboratory.

The present invention also relates to an apparatus for sampling water utilizing solid phase extraction. A sample pump, controlled by a controller, is provided for withdrawing a water sample from a body of water to be sampled. A temporary storage chamber is in fluid communication with the sample pump. A solid phase extraction device, in fluid communication with the temporary sample storage chamber, is provided for extracting an analyte from the water sample. The apparatus can also include a liquid detector for sensing the presence of a water sample at the sample pump and various devices for measuring the quantity of sample passing through the sampler.

BRIEF DESCRIPTION OF THE SEVERAL VIEWS OF THE DRAWINGS

Other objects, advantages, and novel features of the present invention will become apparent from the following detailed description of the invention when considered in conjunction with the accompanying drawings, wherein.

DETAILED DESCRIPTION OF THE INVENTION

Figure 1:
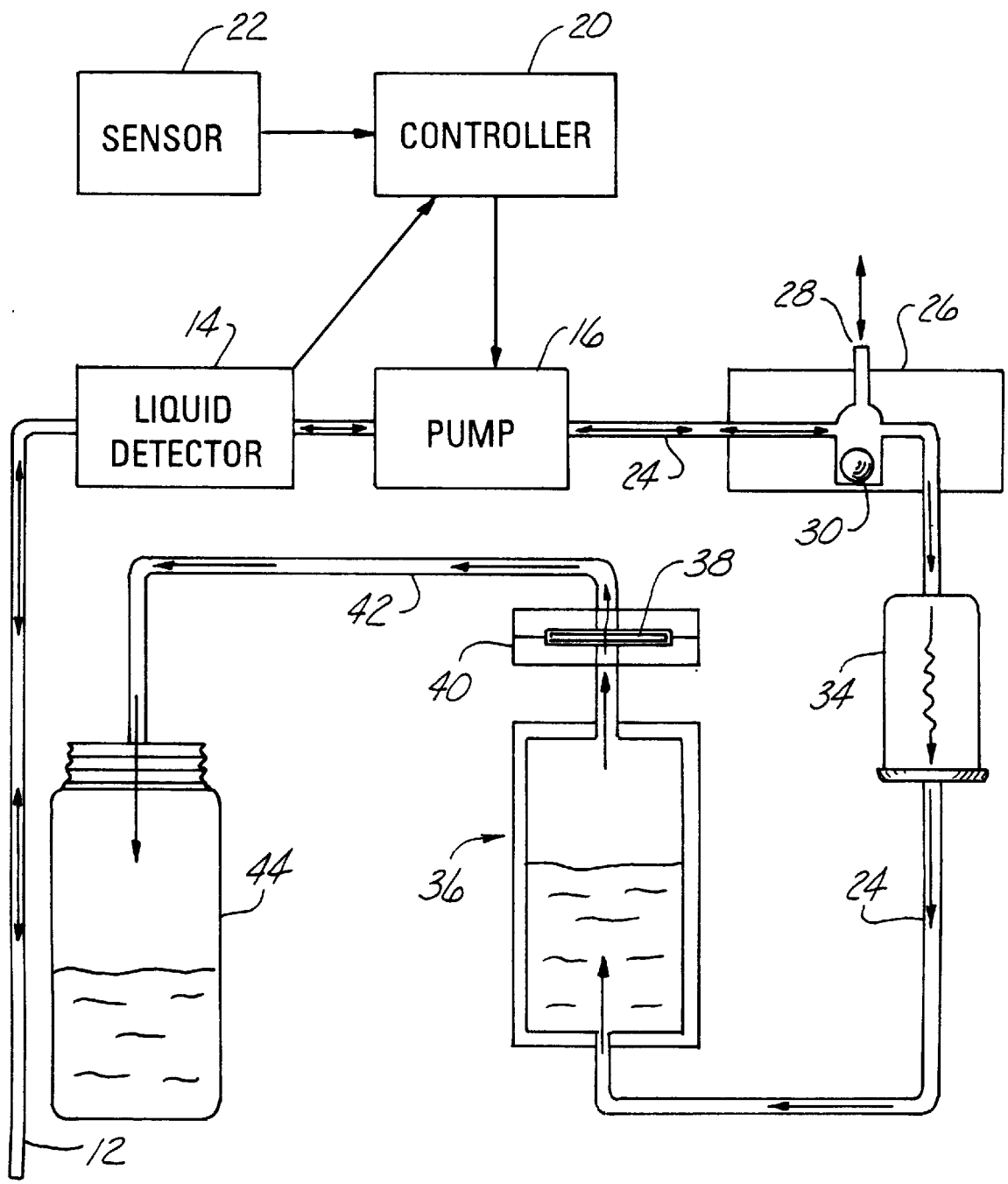
FIG. 1 is a block diagram of a water sampler constructed in accordance with the present invention.

Referring now to the drawings, wherein like reference numerals designate identical or corresponding parts throughout the several views, FIG. 1 depicts a block diagram of the water sampling apparatus of the present invention. The sampling apparatus includes a sample inlet line 12 which passes through a liquid detector 14 and to a reversible peristaltic pump 16. The pump 16 is under the control of a programmable controller 20, which permits sampling and purging at numerous user-definable parameters. The controller 20 receives a signal from the liquid detector 14 as to the presence or absence of a water sample entering or exiting the pump 16 as will be described further below. The controller 20 also receives data from a sensor 22 to be further described below.

Water sample passes from the pump 16 through a sample line 24 to a purge valve 26. When a sample is to be taken, the pump 16 initially draws air through the intake line 12, into the sample line 24, and out the vent 28 of the purge valve 26. When the water sample reaches the purge valve 26, the check ball 30 floats up to close the vent 28 and sample continues through the apparatus. After sample collection, the pump 16 is reversed and draws air into the purge valve 26 through the vent 28, purging that portion of the invention upstream of the purge valve.

After passing through the purge valve 26, the water sample passes through a filter 34 for removal of particulate matter from the sample to prevent obstruction of the solid phase extraction device 40. The sample then enters a temporary sample storage device 36, described in more detail below, where it is pressurized by the pump 16. This temporary storage allows for sample collection at a flow rate which exceeds the maximum flow capability of the solid phase extraction device 40. Under the influence of the pressure build-up within the storage device 36, the sample flows through a solid phase extraction device 40, which in a preferred embodiment utilizes a 47 mm Empore solid phase extraction disk 38 manufactured by 3M®. A solid phase extraction cartridge, also well known in the art, would be suitable as well.

After extraction, the water sample flows through an outlet line 42 and to either a collection bottle 44 or a sample quantity measurement device 60 (FIG. 3), or is discharged to waste, depending on the particular embodiment.

Figure 2:
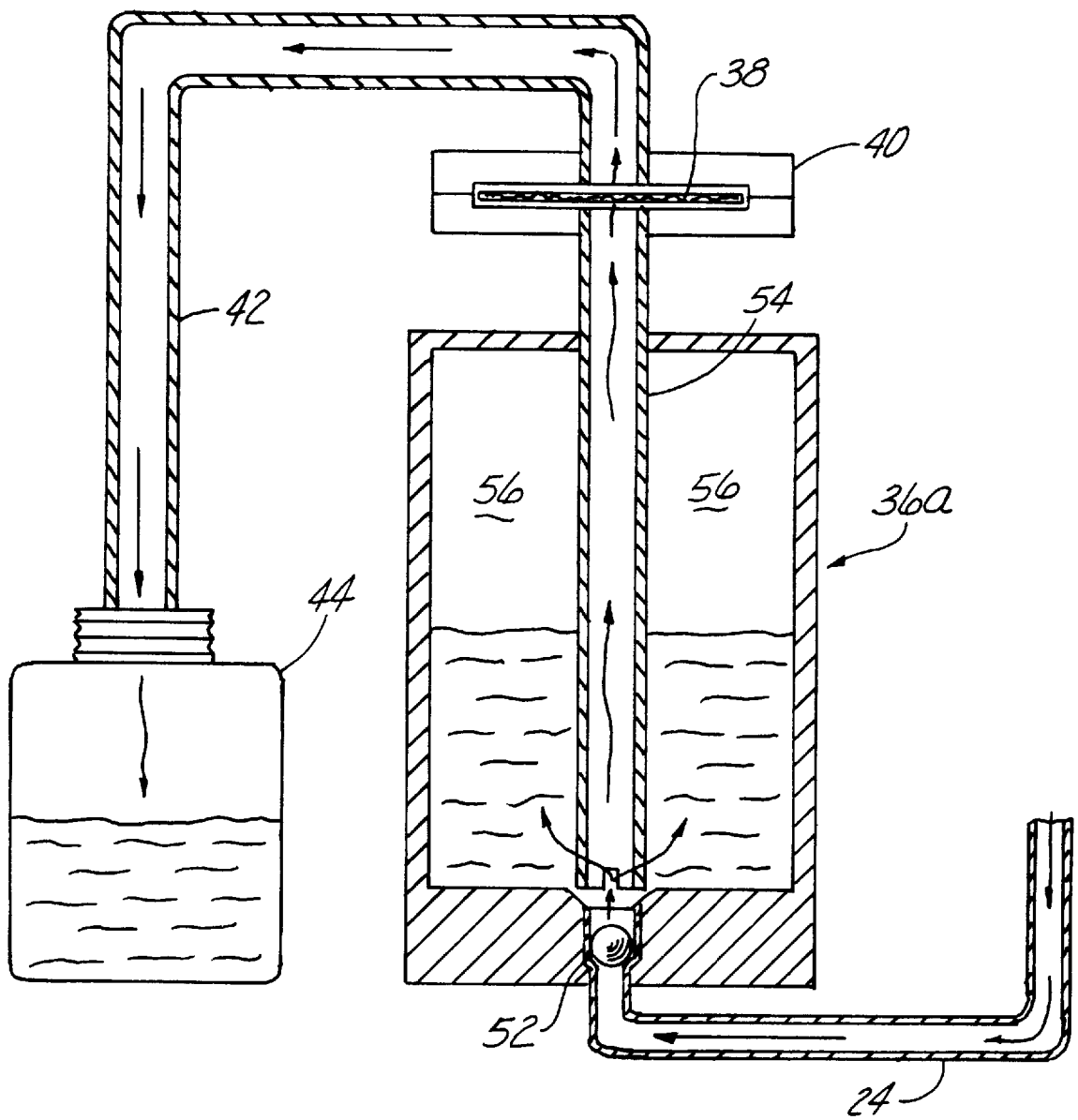
FIG. 2 is a diagrammatic view of a storage device, disk holder, and collection bottle of a first embodiment of the present invention.

Referring now also to FIG. 2, a first embodiment of the temporary sample storage device 36 is depicted and is seen to comprise a compression chamber 36a, a one-way check valve 52 at the input point of sample line 24, and an elongate output tube 54. In this particular embodiment, the controller 20 activates the pump 16 at a programmed time and, upon detection of the presence of the water sample by the liquid detector 14, will command the pump to operate for an additional predetermined number of cycles or an additional predetermined period of time. The water sample will then pass through the purge valve 26, through the filter 34, and past the check valve 52 into the compression chamber 36a where it acts to compress the air 56. When the pump 16 has completed its predetermined number of cycles or pumping time, and has thereby pumped a predetermined quantity of sample into the chamber 36a, it is shut off and the compressed air 56 within the chamber 36a forces the sample up through the output tube 54, through the solid phase extraction device 40, and out the outlet line 42. In the depicted embodiment of FIG. 2, the sample waste is saved in a collection bottle 44 for later measurement of total sample quantity passed through the invention.

Figure 3:
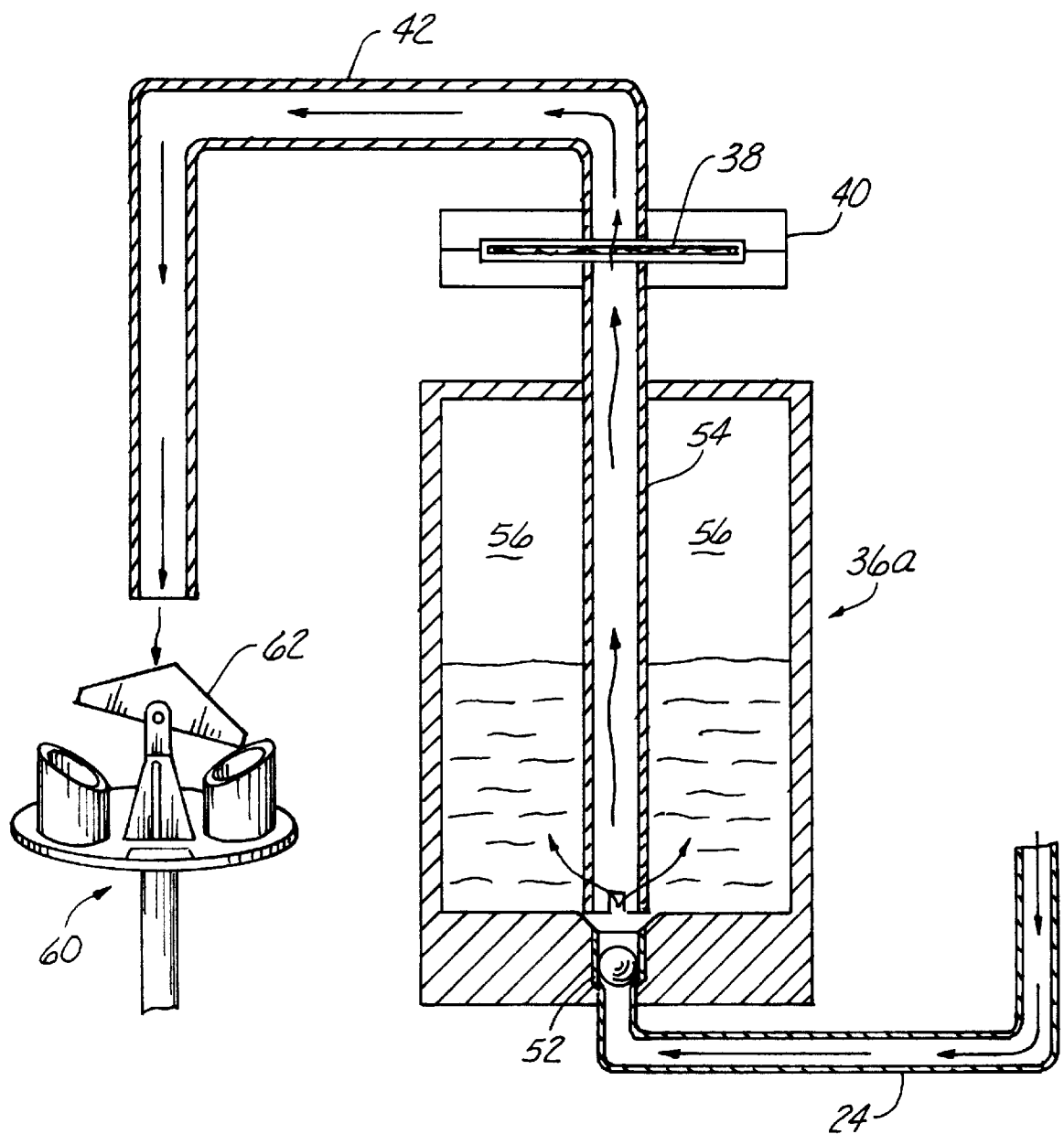
FIG. 3 is a diagrammatic view of a storage device, disk holder, and sample measurement device of a second embodiment of the present invention.

A second embodiment of the invention is depicted in FIG. 3 which utilizes the compression chamber 36a just described, but replaces the collection bottle 44 with a sample quantity measurement device 60. The particular sample quantity measurement device 60 depicted is a Model 674 Rain Gauge, available from Isco, Inc. of Lincoln, Nebr. Each side of the teeter-totter bucket mechanism 62 collects a precise quantity of sample water which then causes the mechanism to tip and dump the collected water to waste. The opposing side of the teeter-totter 62 then collects another precise quantity of water and then tips in the opposite direction. Each tip of the teeter-totter 62 is counted, providing a precise measurement of water sample passing through the apparatus 60. With this precise measurement of the quantity of water sample passing through the sampler, the collection bottle 44 is unnecessary. It should be obvious to one skilled in the art that any precise quantity measurement device may be substituted for the rain-gauge apparatus depicted.

Figure 4:
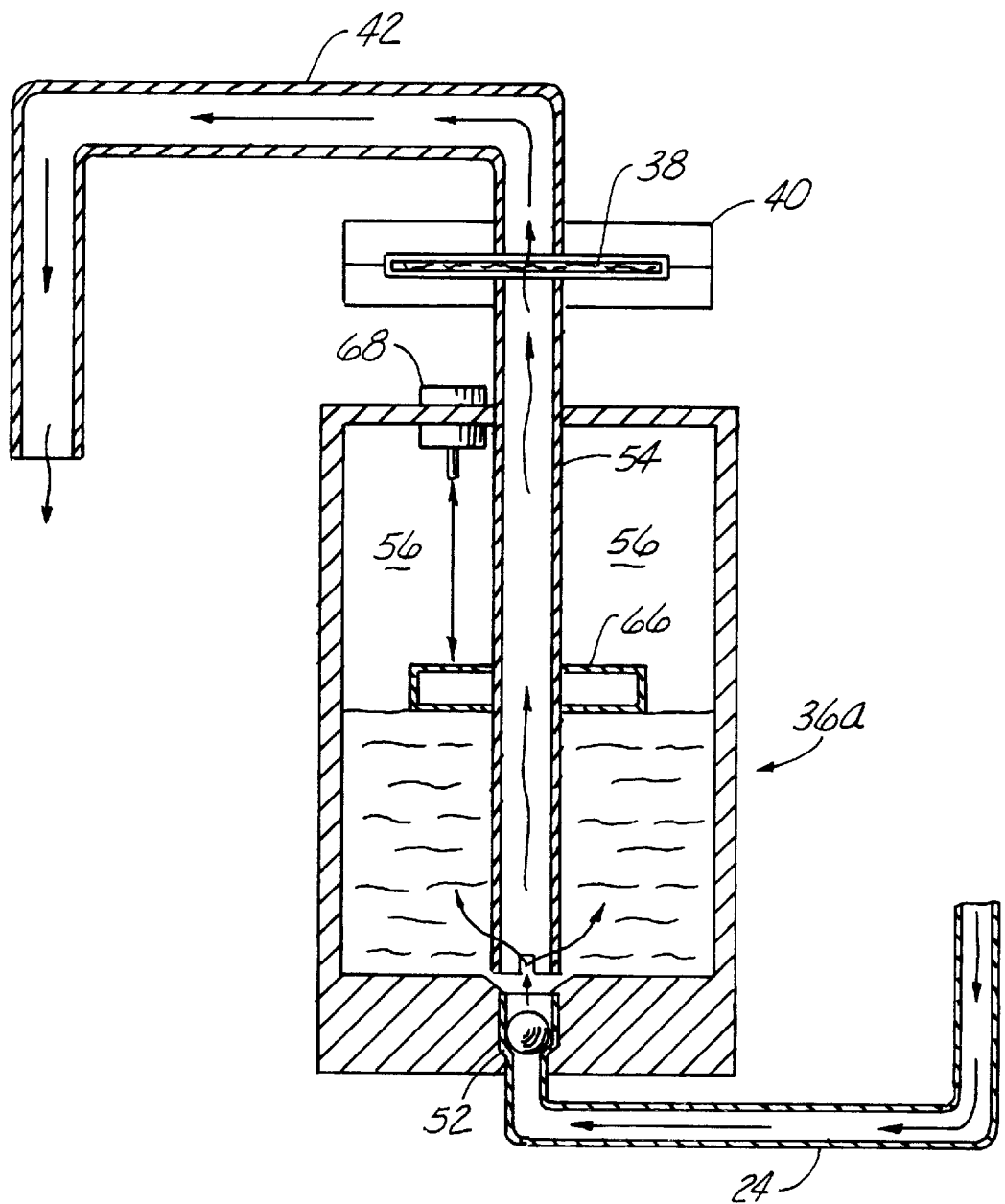
FIG. 4 is a diagrammatic view of a storage device, disk holder, and sample measurement device of a third embodiment of the present invention.

A third embodiment of the invention is depicted in FIG. 4 in which the sensor 22 of FIG. 1 is comprised of a float 66 and switch 68 for precision measurement of water sample quantity passing through the invention. Water sample enters the compression chamber 36a as described for FIG. 2, however in this embodiment the controller 20 shuts off the pump 16 when the float 66 contacts the switch 68. This again provides a precise measurement of the quantity of water sample passing through the invention, rendering the collection bottle 44 unnecessary.

Figure 5:
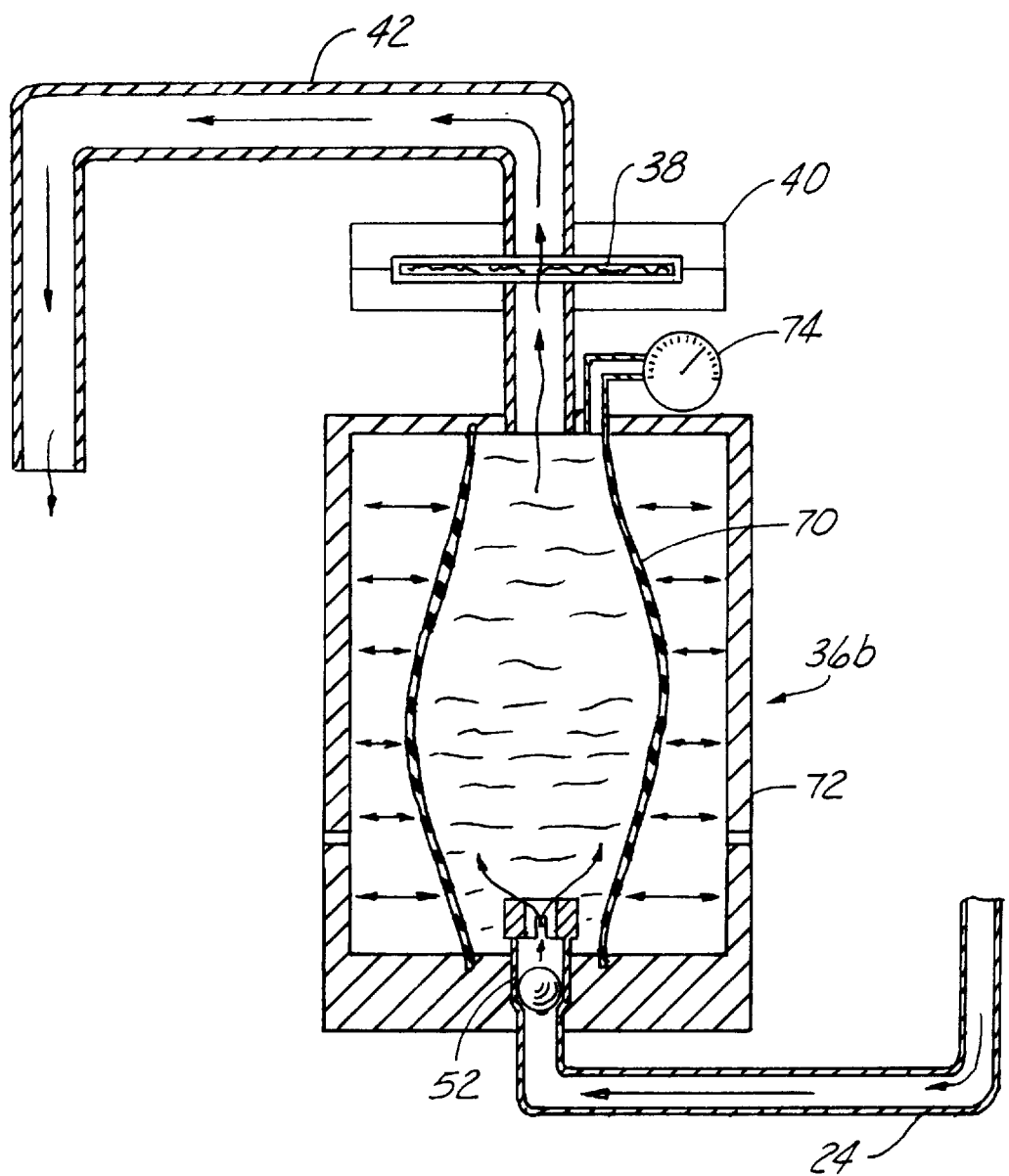
FIG. 5 is a diagrammatic view of a storage device, disk holder, and sample measurement device of a fourth embodiment of the present invention.

A fourth embodiment of the invention is depicted in FIG. 5 wherein the temporary sample storage device 36b is comprised of an elastic tube 70 contained within a vented housing 72. As water sample is pumped into the elastic tube 70 as previously described, the expanding tube puts the sample under pressure which is measured by a pressure sensor 74. At a predetermined pressure, the pressure sensor 74 signals the controller 20 to shut off the pump 16, and the pressurized water sample is then forced through the solid phase extraction device 40. The quantity of water sample passed through the invention may then be determined from the known pressure-expansion ratio of the elastic tube 70.

Figure 6:
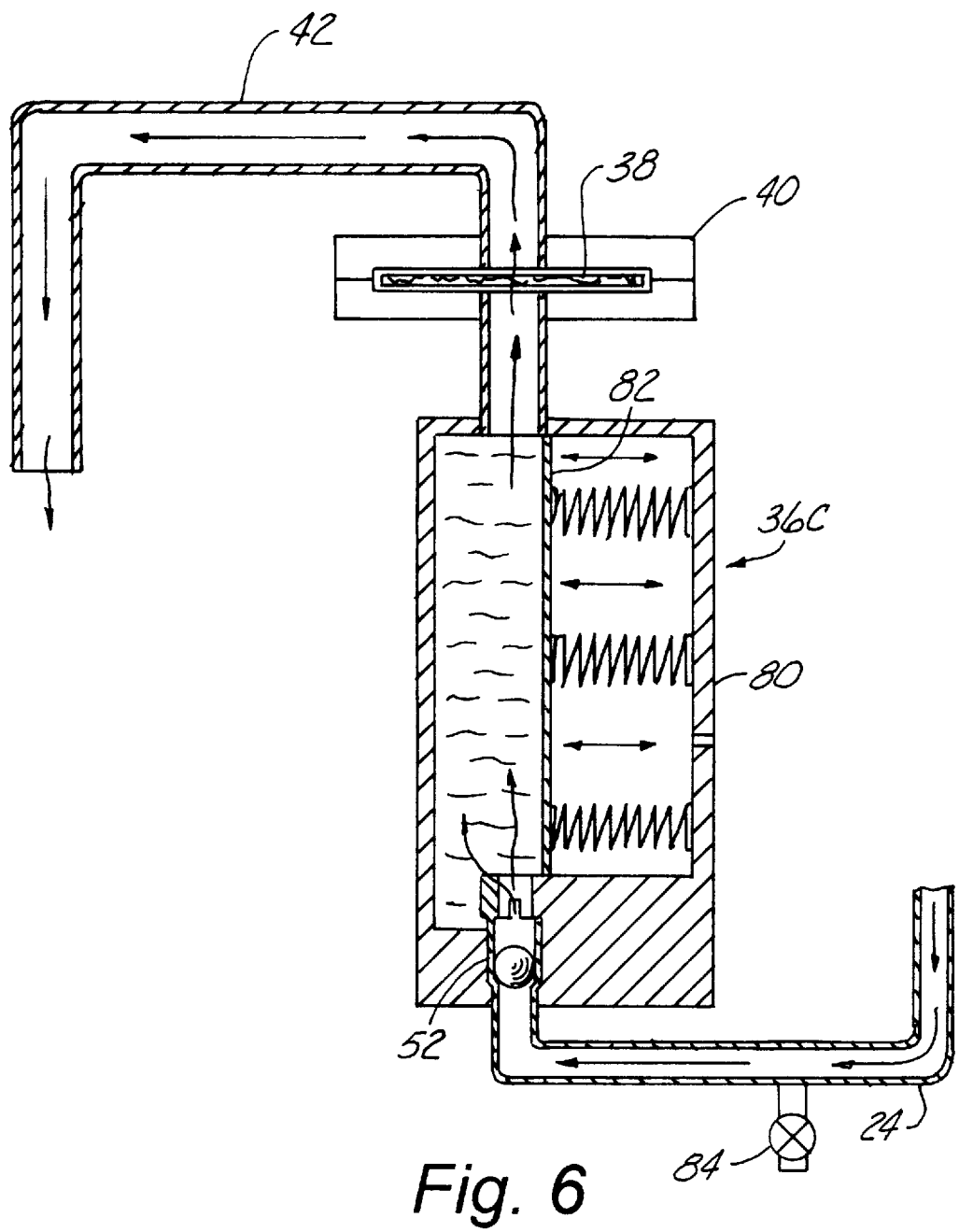
FIG. 6 is a diagrammatic view of a storage device, disk holder, and sample measurement device of a fifth embodiment of the present invention.

A fifth embodiment of the invention is depicted in FIG. 6 wherein the temporary sample storage device 36c is comprised of a vented housing 80 having a moveable wall 82 responsive to the pressurized water sample build up therein.

In this embodiment, the pump 16 is turned on by the controller 20 for a predetermined number of cycles or period of time, known to be in excess of that required to fill and pressurize the sample storage device 36c. When the storage device reaches its predetermined quantity (and therefore pressure) level, a pressure-sensitive bypass valve 84 bleeds water sample to waste until the pump 16 is shut off by the controller 20. The pressurized water sample is then slowly forced through the solid phase extraction device 40 as previously described.

It should be obvious to one skilled in the art that the various embodiments of the temporary sample storage device 36 of the invention and the various embodiments of the sample quantity measurement sensors and devices 22, 60 of the invention may be used in numerous combinations to provide a high collection rate, low extraction rate sampler that eliminates the requirement for water sample collection after extraction.

Although several exemplary embodiments of the invention have been described in detail above, those skilled in the art will readily appreciate that many modifications are possible without materially departing from the novel teachings and advantages of this invention. Accordingly, all such modifications are intended to be included within the scope of this invention as defined in the following claims.

In the claims, means-plus-function clauses are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

What is claimed is:

1. A method for sampling water utilizing solid phase extraction comprising:

quickly withdrawing a water sample from a body of water to be sampled at a collection flow rate within a first period of time;

storing said water sample under pressure in a pressure chamber; and slowly passing said water sample from said pressure chamber through a solid phase extraction device having a maximum flow rate capability which is lower than said collection flow rate within a second period of time, said second period of time being longer than said first period of time.

2. A method for sampling water utilizing solid phase extraction comprising:

quickly withdrawing a water sample from a body of water to be sampled at a collection flow rate within a first period of time;

storing said water sample under pressure in a pressure chamber;

slowly passing said water sample from said pressure chamber through a solid phase extraction device having a maximum flow rate capability which is lower than said collection flow rate within a second period of time, said second period of time being longer than said first period of time; and automatically determining a quantity of water passed through said solids phase extraction device.

* * * * *